United States Patent [19]

Crivello et al.

[11] Patent Number: 5,446,172
[45] Date of Patent: Aug. 29, 1995

[54] METHOD FOR MAKING TRIARYLSULFONIUM HEXAFLUOROMETAL OR METALLOID SALTS

[75] Inventors: James V. Crivello, Clifton Park; Julia L. Lee, Schenectady, both of N.Y.

[73] Assignee: General Electric Company, Schenectady, N.Y.

[21] Appl. No.: 769,520

[22] Filed: Oct. 2, 1991

Related U.S. Application Data

[63] Continuation of Ser. No. 516,408, Apr. 30, 1990, abandoned.

[51] Int. Cl.[6] ............................................. C07D 333/34
[52] U.S. Cl. .................................... 549/62; 549/66
[58] Field of Search ............. 549/62, 66; 568/57, 568/58

[56] References Cited

U.S. PATENT DOCUMENTS 4,161,478   7/1979   Crivello ............................... 568/58
4,173,476  11/1979   Smith et al. .
4,210,552   7/1980   Frenier ................................ 568/58

OTHER PUBLICATIONS

GE CR&D Reprint #8580—Photoinitiated cationic Polymerization with Triarylsulfonium salts—JV Crivello and JHW Lam—Journal of Polymer Science: Polymer Chemistry Edition, vol. 17,977–999 (1979).
GE CR&D Reprint #8434—A New Preparation of Triarylsulfonium and —Selenonium Salts via the Copper (II)—Catalyzed Arylation of Sulfides and Selenides with Diaryliodonium Salts—JV Crivello and JHW Lam—Journal of Organic Chem. 43,3055(1978).

*Primary Examiner*—Alan Siegel
*Attorney, Agent, or Firm*—William H. Pittman

[57] ABSTRACT

A method for making a triarylsulfonium hexafluoro metal or metalloid salt is provided by effecting reaction between a diarylsulfoxide and an aromatic substrate, such as an arylalkylether in the presence of a solution of phosphorus pentoxide and methanesulfonic acid to produce a triarylsulfonium complex. A metathesis of the resulting triarylsulfonium complex is effected with an alkali metal hexafluoro metal or metalloid salt.

3 Claims, No Drawings

METHOD FOR MAKING TRIARYLSULFONIUM HEXAFLUOROMETAL OR METALLOID SALTS

CROSS REFERENCE TO RELATED APPLICATION

This application is a Continuation of application Ser. No. 07/516,408, filed Apr. 30, 1990 now abandoned.

BACKGROUND OF THE INVENTION

Prior to the present invention, various methods were available for making symmetrical and asymmetrical triarylsulfonium salts. For example, P.A.Lowe, Chemistry of the Sulfonium Group, Volume 1, John Wiley, New York, 1981, page 13 and Trost et al, Emerging Synthetic Intermediates, Academic Press, London 1975, provide reviews of synthetic routes for synthesizing triarylsulfonium salts. Smith et al, U.S. Pat. No. 4,173,476, shows a procedure for preparing a triarylsulfonium complex using a mixture of diphenylsulfoxide, diphenylsulfide, and phosphorus pentoxide. Although procedures such as Smith et al provide complex triarylsulfonium salts, the 44% yield of the salt is relatively low, and the range of substrates which can be used is extremely limited. In addition, Smith et al's reaction mixture is heterogeneous due to the insolubility of the phosphorus pentoxide. Further, workup is complicated by the slow hydrolysis of the sticky mass of excess phosphorus pentoxide, products and starting materials.

In an improved procedure for making triarylsulfonium complexes, a strong acid, such as sulfuric acid, is used in combination with an oxidizing agent, such as peracetic acid and a dehydrating agent, for example acetic anhydride to produce in-situ, a mixture of a diarylsulfide and diarylsulfoxide. This mixture can be converted to the corresponding trirarylsulfonium acid complex followed by metathesis to the corresponding hexafluorometal or metalloid salt. Although effective results can be obtained using a strong acid, such as sulfuric acid, lower yields can be expected due to the sulfonation of the substrate as a competing side reaction.

SUMMARY OF THE INVENTION

The present invention is based on the discovery that symmetrical and asymmetrical triarylsulfonium complexes can be made in excellent yields by effecting the condensation of arylsulfoxides with aromatic compounds in the presence of a solution of phosphorus pentoxide (PP) and methanesulfonic acid (MSA), or "PP/MSA". It has been found that the sulfonation reaction proceeds particularly well in instances where an activated aromatic compound i.e., a compound activated by electron donor substitutents is used in combination with the arylsulfoxide. Conversion of the triarylsulfonium complex to the corresponding hexafluorometal or metalloid salt, can be achieved by a metathesis reaction with an alkali metal or metalloid hexafluoro salt. A preferred procedure for making such triarylsulfonium hexafluorometal or metalloid salts is shown by the following equation where the triarylsulfonium complex is not shown separately as it is produced in-situ and not isolated,

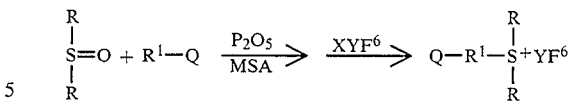

R and $R^1$ are selected from the same or different $C_{(6-13)}$ monovalent aromatic organic radicals, Q is a group capable of activating $R^1$ such as a $C_{(1-8)}$ alkoxy radical, X is an alkali metal ion, Y is a Group VA or VIA metal or metalloid, and MSA is methanesulfonic acid.

STATEMENT OF THE INVENTION

There is provided by the present invention a method for making triarylsulfonium hexafluorometal or metalloid salt which comprises, (1) effecting reaction between a diarylsulfoxide and a member selected from the class consisting of a thiophene, an arylalkyl ether, an arylalkyl thioether and a polyarylsulfide in the presence of an effective amount of a solution of phosphorus pentoxide in methanesulfonic acid to produce a triarylsulfonium complex, (2) effecting the metathesis of the triarylsulfonium complex of (1) with an alkali metal hexafluoro metal or metalloid salt, and (3) recovering a triarylsulfonium hexafluoro metal or metalloid salt from the mixture of (2).

Some of the diarylsulfoxides which can be used in the practice of the present invention are, for example, diphenylsulfoxide, ditolylsulfoxide, dibenzothiophene-S-oxide, 4,4'-dichlorodiphenylsulfoxide, and (4-methylphenyl) phenylsulfoxide.

Thiophenes which can be used as substrates in the practice of the present invention are, for example, thiophene, 2-methylthiophene, 3-methylthiophene, 3,4-dimethylthiophene, 2-chlorothiophene, benzothiophene, 3-chlorothiophene, thiophene-3-carboxylic acid.

Polyarylsulfides which preferably include diarylsulfides or triarylsulfides, also can be used as substrates in the practice of the present invention. For example,there can be used diphenylsulfide, (4-methylphenyl) phenylsulfide dibenzothiophene, (2-methylphenyl) phenylsuflide, 2,2'-ditolylsulfide, (3-chlorophenyl) phenylsulfide, and bis(1,4-thiophenoxy)benzene.

Arylalkylether and arylalkylthioethers also can be used as substrates in the practice of the invention. Preferably, anisole, anethole, n-propoxybenzene, i-propoxybenzene, t-butoxybenzene, n-butoxybenzene, i-butoxybenzene, n-amyloxybenzene, i-amyloxybenzene, n-hexyloxybenzene, 2-ethylhexyloxybenzene, and n-octyloxybenzene can be employed.

In the practice of the present invention, condensation of the diarylsulfoxide and the aromatic substrate, which hereinafter means, a thiophene, an arylalkyl ether, or polyarylsulfide or mixture thereof, as previously defined can be effected at temperatures in the range of from 0° C. to 100° C. in the presence of PP/MSA which hereinafter means a solution of phosphorus pentoxide in methanesulfonic acid. Substantially equal molar amounts of the diarylsulfoxide and aromatic substrate are preferably used in the formation of the triarylsulfonium complex. However, a variation of 1 to 3 moles of the diarylsulfoxide, per mole of the aromatic substrate will provide effective results.

Preferably PP/MSA constitutes about 1 part by weight of phosphorus pentoxide, per 10 parts by weight of methane sulfonic acid. Depending upon the nature of the substrate and the degree of agitation, reaction times can be from 1 to 10 hours. The triarylsulfonium complex does not have to be isolated from the mixture. It can be directly combined with water followed by the addition of alkali metal hexafluorometal or metalloid salt to effect a metathesis reaction. Recovery of the aforementioned triarylsulfonium hexafluorometal or metalloid salt can be effected by standard techniques, such as filtration, decantation, or recrystallization from an organic solvent, such as, ethanol, or dichloromethane.

The triarylsulfonium hexafluorometal or metalloid salts made in accordance with the present invention can be used as a photoinitiator in effecting the photopolymerization of various organic materials, such as, epoxy resins, cyclic ethers, and cationically polymerizable organic materials, such as aliphatically unsaturated compounds, such as, styrene, α-methylstyrene etc.

In order that those skilled in the art will be better able to practice the present invention, the following examples are given by way of illustration and not by way of limitation. All parts are by weight unless otherwise indicated.

Example 1

A solution of phosphorus pentoxide in methanesulfonic acid (PP/MSA) was prepared by initially fractionally distilling methanesulfonic acid under reduced pressure (bp 110° C./1 torr). There was added 69.1 grams of phosphorus pentoxide, which had been ground to a powder to 691.4 grams of the fractionally distilled methanesulfonic acid. The resulting mixture was stirred and warmed periodically to effect the dissolution of the phosphorus pentoxide into the methanesulfonic acid.

There was added to 20 ml of the above PP/MSA solution, 5.05 grams (0.025 mole) of diphenylsulfoxide, and 2.7 grams (0.025 mole) of anisole. The mixture was stirred at 50° C. for 1.5 hours. The mixture was poured into 200 ml of water. A dark oil was obtained. There was added to the water-oil mixture, 13.0 grams of sodium hexafluoroantimonate resulting in the production of a precipitate. The product was stirred, filtered, washed with water and dried. There was obtained an 87% yield of a crude triarylsulfonium hexafluoroantimonate salt. Further purification was effected by washing with ether and recrystallizing the product from ethanol. Based on method of preparation, the product was diphenyl(4-methoxyphenyl)sulfonium hexafluoroantimonate having a melting point of 135°–136° C. The pure sulfonium salt was recovered at a 80% yield. A 1 mil film of a solution of 1% of the sulfonium salt in 4-vinylcyclohexene dioxide was irradiated with a GE H3T7 medium pressure mercury arc lamp. A tack-free film was obtained in 1–2 seconds.

Example 2

A mixture of 12.12 grams (0.06 mole) of diphenylsulfoxide, 10.3 gram of octylphenyl ether and 20 ml of PP/MSA resulted in an exothermic reaction. The temperature of the mixture increased to 42° C. After the exotherm had subsided, the temperature was raised to 50° C. and maintained at that temperature for 1 hour with stirring. There was obtained a complex reaction product of diphenylsulfoxide and octylphenyl ether. The mixture was then poured into 200 ml of water. A clear yellow solution was obtained. There was added to the solution, 9.5 grams of potassium hexafluorophosphate. A yellow oil precipitated from the solution which solidified to a white crystalline solid upon standing. The mixture was warmed slightly to 40° C. and stirred. There was obtained a quantitative yield of crude product. The product was recovered by filtering and washed twice with water followed by petroleum ether. The crude product was further purified by recrystallization from absolute ethanol. (4-octyloxyphenyl)diphenylsulfonium hexafluorophosphate was obtained at a 74% yield. It had a melting point of 94°–95° C.

Example 3

There was added to 12.12 grams (0.06 mole) of diphenylsulfoxide, 9.3 grams (0.05 mole) of diphenylsulfide and 20 ml of PP/MSA. Exothermic reaction occurred with a temperature rising to 74° C.. After about 3 minutes, the initial purple color of the solution turned yellow. The solution was maintained. at 40°–45° C. for 1 hour to complete the formation of a complex reaction product. The reaction mixture was then poured into 200 ml of water followed by the addition of 9.5 grams of potassium hexafluorophosphate. The mixture was then stirred for 1 hour and a white crystalline product was filtered off, washed with water and dried. There was obtained a 91.4% yield by recrystallization from absolute ethanol of diPhenyl(4-thiophenoxyphenyl)sulfonium hexafluorophosphate.

Example 4

There was added 20 ml of the PP/MSA solution to a mixture of 10.1 grams (0.05 mole) of diphenylsulfoxide and 4.2 grams (0.05 mole) of thiophene. The resulting mixture exothermed to 50° C. and became viscous and purple in color. After 0.5 hours, the blue reaction mixture was poured into 200 ml of water. A very dark colored solution was obtained. It was added to the solution, 9.2 grams (0.05 mole) of potassium hexafluorophosphate. A dark colored solid was obtained. The solid was isolated by decantation and washed several times with fresh water and then filtered. The solid was dissolved in dichloromethane and passed through a column of neutral alumina. A pale yellow crystalline solid was obtained upon evaporation of the solvent. It was recovered, 10.6 grams for a 51.2% yield of diphenyl (2-thiophenyl) sulfonium hexafluorophosphate having a melting point of 177°–173° C. Elemental analysis showed; Calculated: % carbon 46.30; % hydrogen 3.14; % sulfur 15.46; Found: % carbon 46.80; % hydrogen 3.12; % sulfur 15.75.

1% solution of the sulfonium salt and 4-vinylcyclohexene dioxide was applied onto a substrate at a 1 mil thickness. The film was exposed to a GE H3T7 medium pressure mercury arc lamp and a cured transparent insoluble, crosslinked film was obtained after an irradiation of 2 seconds.

Example 5

The procedure of Example 1 was repeated except that in place of anisole other phenyl ethers were used to form triarylsulfonium complexes. In addition, other alkali metal hexafluorometalloid salts were substituted for sodium hexafluoroantimonate. The following results were obtained where Y is a metal or metalloid:

TABLE 1

Triarylsulfonium Hexafluorometal or metalloid Salts

| Substrate | YF$_6$ | Yield (%) | M.P. (°C.) | | % C | % H | % S |
|---|---|---|---|---|---|---|---|
| C$_6$H$_4$OCH$_3$ | SbF$_6$— | 87 | 135–136 | C: | 43.10 | 3.21 | 6.06 |
| | | | | F: | 43.02 | 3.41 | 6.02 |
| C$_6$H$_4$OCH$_3$ | PF$_6$— | 90.4 | 143–145 | C: | 52.05 | 3.88 | 7.31 |
| | | | | F: | 51.46 | 4.02 | 7.51 |
| C$_6$H$_4$OCH$_3$ | AsF$_6$— | 88 | 143–145 | C: | 47.30 | 3.53 | 6.64 |
| | | | | F: | 47.11 | 3.59 | 7.01 |
| C$_6$H$_4$OC$_2$H$_5$ | PF$_6$— | 76 | 102–103 | C: | 53.10 | 4.20 | 8.08 |
| | | | | F: | 53.40 | 4.31 | 7.56 |
| C$_6$H$_4$OC$_8$H$_{17}$ | PF$_6$— | 74 | 95–97 | C: | 58.21 | 5.78 | 5.97 |
| | | | | F: | 58.21 | 5.80 | 6.10 |
| C$_6$H$_4$OC$_{10}$H$_{21}$ | SbF$_6$— | 50 | 65–71 | C: | 51.30 | 5.34 | 4.89 |
| | | | | F: | 51.27 | 5.44 | 5.59 |
| C$_6$H$_4$OC$_{10}$H$_{21}$ | PF$_6$— | 99 | 103–105 | C: | 59.57 | 6.21 | 5.67 |
| | | | | F: | 59.74 | 6.32 | 6.00 |
| C$_6$H$_4$OC$_{12}$H$_{25}$ | SbF$_6$— | 76 | 79–82 | C: | 52.71 | 5.71 | 4.69 |
| | | | | F: | 52.70 | 5.89 | 4.92 |
| C$_6$H$_4$OC$_{18}$H$_{37}$ | SbF$_6$— | 98 | 90–95 | C: | 56.32 | 6.65 | 4.17 |
| | | | | F: | 56.02 | 6.79 | 4.92 |
| C$_6$H$_4$OC$_6$H$_5$ | PF$_6$— | 76 | 110–111 | C: | 57.60 | 3.80 | 6.40 |
| | | | | F: | 57.31 | 3.86 | 6.77 |

Although the above examples are directed to only a few of very many triarylsulfonium hexafluoro metal or metalloid salts which can be made in accordance with the practice of the present invention, it should be understood that the present invention is directed to the synthesis of a much broader variety of triarylsulfonium hexafluoro metal or metalloid salts resulting from the use of a solution of diarylsulfoxide in methanesulfonic acid to facilitate reaction between diarysulfoxide and a suitable substrate to produce a triarylsulfonium complex followed by the metathesis of the resulting diarylsulfonium salt and alkali metal or metalhexafluoro salts as shown in the description preceding these examples.

What is claimed is:

1. A method for making a diarylthienylsulfOnium hexafluorometal or metalloid salt which comprises,
    (1) effecting reaction between a diarylsulfoxide and a thiophene in the presence of an effective amount of a solution of phosphorus pentoxide in methanesulfonic acid to produce a diarylthienylsulfonium complex,
    (2) effecting the metathesis of the diarylethienylsulfonium complex of (1) with an alkali metal hexafluorometal or metalloid salt, and
    (3) recovering a diarylthienylsulfonium hexafluorometal or metalloid salt from the mixture of (2).

2. A method in accordance with claim 1 where the alkali metal hexafluoro metal or metalloid salt is sodium hexafluoroantimonate.

3. A method in accordance with claim 1 where the alkali metal hexafluoro metal or metalloid salt is sodium hexafluorophosphate.

* * * * *